United States Patent [19]

Heusler et al.

[11] 4,252,617

[45] Feb. 24, 1981

[54] METHOD AND APPARATUS FOR SPECTROPHOTOMETRY

[75] Inventors: Konrad Heusler, Einersberger Blick 21, 3392 Clausthal-Zellerfeld, Fed. Rep. of Germany; Heiner Debrodt, Clausthal-Zellerfeld, Fed. Rep. of Germany

[73] Assignee: Konrad Heusler, Fed. Rep. of Germany

[21] Appl. No.: 930,127

[22] Filed: Aug. 1, 1978

[30] Foreign Application Priority Data

Aug. 4, 1977 [DE] Fed. Rep. of Germany ....... 2735247

[51] Int. Cl.³ .................. G01N 21/25; G01N 27/00
[52] U.S. Cl. .............................. 204/1 T; 204/195 R; 356/412
[58] Field of Search .................. 204/1 T, 195 R; 356/412

[56] References Cited

PUBLICATIONS

James E. McClure, Anal. Chem., vol. 42, No. 4, pp. 551–552, Apr. 1970.

*Primary Examiner*—G. L. Kaplan
*Attorney, Agent, or Firm*—Steele, Gould & Fried

[57] ABSTRACT

Method and apparatus for spectrophotometric investigation of products of electrochemical reactions in which a solution containing at least one dissolved initial product is directed essentially axially towards a rotating disc electrode surrounded by an optically translucent ring, the flow being reversed at the rotating electrode into an outwardly directed radial flow, and the concentration of the products formed at the electrode being determined by passing monochromatic light through the radial product flow and the optically translucent ring and by measuring the light absorption, wherein the measurement is performed under quasi-stationary conditions in that the current for the electrochemical reaction is permitted to flow without interruption for at least approximately 0.5 seconds before the measurement is performed.

37 Claims, 8 Drawing Figures

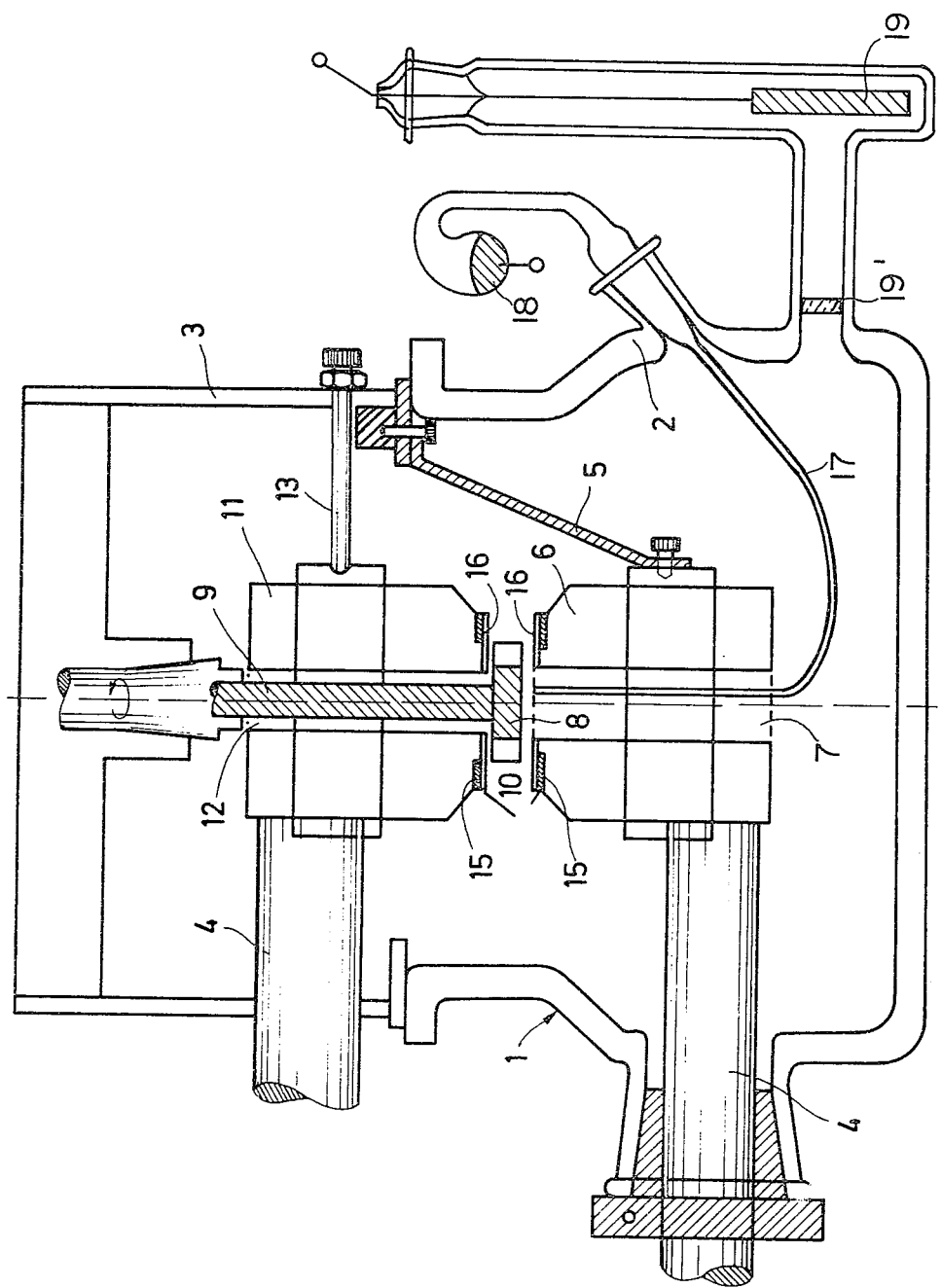

METHOD AND APPARATUS FOR SPECTROPHOTOMETRY

BACKGROUND OF THE INVENTION

The invention relates to a method for the spectrophotometric investigation of products of electrochemical reactions in which a solution containing at least one dissolved initial product is directed essentially axially towards a rotating disc electrode surrounded by an optically translucent ring, the flow being reversed at the rotating electrode into an outwardly directed radial flow, and the concentration of the products formed at the electrode being determined by passing monochromatic light through the radial product flow and the optically translucent ring and by measuring the light absorption, as well as to an apparatus for performing the method.

A method and an apparatus for the spectrophotometric investigation of electrochemically generated products is known from a publication in "Analytical Chemistry", Vol. 42, No. 4, pp. 551 and 552, 1970. A rotating electrode having a vertical rotation axis projects into a vessel below the surface of a solution used to perform the electrochemical reaction. The electrode has a working surface which is perpendicular to the rotation axis and which on the outer periphery of the working surface is surrounded by a number of optical fibres. The optical fibres are embedded in a cured synthetic resin and, after reversal in tapered manner into the direction of the rotation axis, pass together with the current lead to the electrode through the bearing of the rotating electrode and up to a light detector. Current lead and optical fibre cable are conducted through a stainless steel tubing providing the shaft which is guided in the bearings. An optical fibre cable for monochromatic light serving as the transmitter terminates at the bottom of the vessel and is directed coaxially to the rotation axis of the electrode with the optical fibres surrounding it. This apparatus is used employing the so-called lock-in technique. The electrical potential of the working electrode is cyclically changed with square pulses. In order to obtain reliable results with this technique, frequencies of at least approximately 10 Hz are usually selected. This technique and this apparatus permit approximate conclusions to be drawn on the course of chemical reactions. However, it is pointed out that considerable noise and low absorption values impair the precision of the investigations.

BRIEF SUMMARY OF THE INVENTION

The task of the invention is to provide a method and an apparatus supplying highly informative results and permitting investigations of both long and short lived primary and secondary products.

This problem is solved by the method of the invention wherein the measurement is performed under quasi-stationary conditions in that the current for the electrochemical reaction is permitted to flow without interruption for at least approximately 0.5 seconds and only then is the measurement performed. It has been found that the inexact results of the known method can, inter alia, be attributed to the fact that the above-described lock-in technique is used. The short pulses only produce a small modulation of the measuring effect because the characteristic times for establishing stationary product concentrations in the boundary layer usually are significantly longer than the pulse times mentioned above. Thus, with the known method regularly only an effect of the second order is measured the magnitude of which does not, in general, permit conclusions to be drawn on the course of the reaction and which has a correspondingly low information value. As opposed to this, the invention works at quasi-stationary conditions. The characteristic times for establishing stationary product concentrations depend on the type of reaction, so that preferably no measurement is made before the current has been switched on for about one second. The measurements can be performed without subsequent switching off of the current. However, preference is given to working with current or voltage pulses lasting approximately 1 to 5 seconds in order to allow the determination of light absorption at zero current during the time intervals between the pulses. These determinations of zero points are particularly advantageous if in the case of relatively long reaction times a stable product is accumulated in the electrically conducting solution so that measuring errors would occur by not taking into account this effect.

It was also recognised that the thickness of the liquid layer penetrated by the light should preferably have certain ratios to the thicknesses of the Prandtl flow boundary layer at the electrode, and particularly of the Nernst diffusion boundary layer at the electrode in order to eliminate further sources of error. The liquid layer must be sufficiently thick for not influencing the Prandtl boundary layer at the surface of the disc. Depending on the viscosity of the liquid and the rotational speed of the rotating disc, this layer has a thickness of approximately 1/10 mm or less. On the other hand, the thickness of the liquid layer should also be as small as possible compared to the thickness of the Nernst boundary layer, so that absorption due to a product formed during the reaction in the bulk of the solution still obeys a sensible relationship to the absorption within the Nernst boundary layer, within which the product formed during the electrochemical reaction stays initially. As the Nernst boundary layer is an order of magnitude smaller than the Prandtl boundary layer and the concentration of the product is usually about 10,000 times higher within the Nernst boundary layer than in the solution, the thickness of the liquid layer penetrated by light can be kept about 100 times greater than the Nernst boundary layer and approximately 10 times greater than the Prandtl boundary layer, if it is intended that the zero displacement of the absorption due to accumulation of the product in the solution remains in the percentage range. Usually the liquid layer thickness is kept in the range of approximately 1 to 10 mm, preferably 2 to 5 mm.

The rotational speed of the electrode can be varied within wide limits. The lower limiting value should be approximately ½ to 1 r.p.s. so that the natural convection of the solution is overcome and the theoretically calculable flow is established at the rotating disc. If the rotational speed is greatly increased the diffusion flow through the Nernst boundary layer rises accompanied by a reduction in the thickness of the said layer, and as a result there is a reduction in the quantity of product to be determined and also a reduction in the absorption values. Therefore, the upper limit is not fixed and is determined by the desired precision of the measurements. Usually speeds of 100 r.p.s. are not exceeded. Other parameters such as current intensity, temperature, concentration of the solution and wave length of the monochromatic light can be adapted to the reaction under investigation.

It is a disadvantage of the initially described known apparatus that the fibres or the optical cable formed therefrom conducting the light from the electrode zone to the receiver zone rotate together with the electrode. Thus, slight local differences in the arrangement of individual fibres in the fibre bundle and in the light guide generate excessive noise due to the rotation relative to the fixed receiver.

However, in the apparatus according to the present invention it is ensured that the optical parts rotating with the electrode are kept very short in the direction of the optical path compared to the known apparatus, whereby in particular due to straight line guidance and plane-parallel formation of the inlet and outlet surfaces, optical errors which could be caused by the rotation of the translucent ring are essentially excluded. In addition, the ring is preferably made from an optically uniform material as opposed to the synthetic resin-bound optical fibres of the known apparatus. In many solutions the use of the known apparatus is limited by the chemical instability of the synthetic resin. Most synthetic resins are not, for example, stable towards alkaline solutions.

In the apparatus according to the present invention the optically translucent ring fixed to the rotating electrode is constructed as a plane-parallel and optically compact ring and there is a jointless and planar transition to the precisely circular outer edge of the electrode. The optically translucent ring is preferably made from quartz glass as well as the remaining optically conductive parts of the apparatus, so that it is possible to work in the ultra-violet range.

The diameter of the metallic disc electrode can be varied according to the particular requirements. In the case of electrodes with a diameter in excess of 10 mm it is advantageous for the electrode to be annular, i.e. with an insulator in the center of the electrode. As a result, for a given current density the current and therefore the consumption of the initial product can be kept low. Moreover, the paths of the products formed during the electrochemical reaction are not undesirably long prior to reaching the optically translucent ring where the optical measurement is performed. A number of products can be investigated simultaneously by measuring at more than one wave length of light.

BRIEF DESCRIPTION OF THE DRAWINGS

The invention is described in greater detail hereinafter relative to non-limitative embodiments and with reference to the attached drawings which show:

FIG. 1, a diagrammatic representation of an embodiment of the apparatus according to the invention;

DETAILED DESCRIPTION OF THE PREFERRED EMBODIMENTS

Figure 2A:
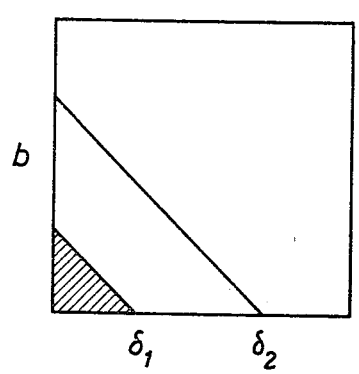
FIG. 2, a diagram of the course of the concentration perpendicular to the rotating disc electrode for two thicknesses $\theta_1$ and $\theta_2$ of the diffusion layer.

In the embodiment of the invention shown in FIG. 1, a reaction vessel 1 is provided which comprises a cup-shaped lower part 2 and an attachment 3 in the form of a cover. The cup-shaped lower part has a laterally sealable opening for passing through an optical cable 4 from a monochromator. Optical cable 4 issues into a circular lamp 6 held by an adjustable mounting support 5. Lamp 6 serves as a transmitter directing the light vertically upwards. The circular lamp 6 in the center provides a free passage 7 and within the cup-shaped lower part is positioned so far above the base that the reagent solution can flow upwards from the bottom through the passage. Coaxially to the circular lamp and above the latter is arranged a rotating disc electrode 8 with a vertical rotation axis, the drive shaft 9 of which passes upwards through cover 3. The diameter of the disc electrode essentially corresponds to the internal diameter of passage 7 in circular lamp 6. The outer periphery of the disc electrode is surrounded by a plane-parallel quartz ring 10 arranged above the light exit of circular lamp 6.

An annular receiver 11 is held by cover 3 and is arranged above quartz ring 10 in essentially mirror-inverted manner with respect to circular lamp 6. Through the coaxial passage 12 of receiver 11 passes the drive shaft 9. Receiver 11 is fixed in the reaction vessel by an adjustable mounting support 13 in the same way as circular lamp 6. An optical cable 4 connected to a light detector passes from receiver 11 through the wall of cover 3.

The reaction vessel can be made from glass. However, it can also be manufactured from high grade steels, when it can simultaneously form the counter-electrode to ring electrode 8. The remaining electrodes, such as the reference electrode and the electrical contact to the rotating electrode are also shown. The counter-electrode 19 is located in a compartment separated from the main cell by a porous glass disc 19'. The reference electrode 18 is connected by a flexible capillary tube 17 filled with an electrolyte. The surface of the light exit at the transmitter and/or circular lamp 6 and the entry surface of receiver 11 are bounded by diaphragms 15. The two diaphragms can be replaced by a thin optically opaque layer, e.g. of metal, on the quartz ring. In addition, said surfaces are also covered by flat quartz rings 16 which provide a chemically stable light entry and exit surface and protect the parts located behind them.

In the present embodiment the oxidation of N,N'-diphenylbenzidine is investigated as an example and the following procedure is used:

For the purpose of the measurements a rotating disc electrode was employed made from platinum-iridium alloy with 10% by weight of iridium. The disc electrode with a radius of r=6.5 mm was the polished end face of a cylinder, screwed with a thread to the drive shaft. The electrode was surrounded by a quartz ring with an external radius r=10 mm and a thickness d=5 mm. With a tolerance of 10 μm the inner bore was adapted to the outer sheath of the electrode. The flat surfaces of the quartz ring had a plane-parallel optical polish. The rotating disc was driven through a 1:2 step-down or step-up gearing by a 30° stepping motor the speed of which was regulated between 1.5 and 120 Hz by special electronics. The drive system and the shaft of the rotating disc electrode were connected by a contact-free magnet coupling. This prevented the transmission of vibrations from the drive to the electrode system. The upper part of the rotary shaft was hollow. The electrical contact from the rotating system to the static system was provided by a mercury drop and an iron wire projecting into the opening of the hollow shaft.

A glass cell with flat fitting was fixed to the electrode mounting support in airtight manner by means of a Teflon seal. A nitrogen flow was passed through the cell by means of gas inlet and outlet capillaries. The counter electrode comprising a 2 cm² platinum foil was located in a second vessel separated from the main vessel by a frit. The connection to the reference electrode was formed by a salt bridge terminating below the disc electrode.

The cell was filled with an electrolytic solution so that the liquid level was 2 to 3 mm below the static disc electrode.

To provide protection against the solvent, the optical components were covered with Teflon. The mounting supports, adjusting mechanism and diaphragm were made from stainless steel. Monochromatic light from a spectrophotometer (M 635, Varian) passed via the optical cable to the circular lamp. The glass fibres used for this purpose pass light in the wave length range 360–800 $\eta$m. The glass fibres arranged in annular manner at the light exit were covered with a thin quartz ring. A gap 2 to 5 mm high was provided between the circular lamp and the rotating disc. The circular lamp had a hollow core with a radius of 6.5 mm. The dimensions of gap and core are selected in such a way that the liquid flow to the rotating disc is virtually not disturbed.

The base electrolyte was 0.1 M LiClO$_4$ in acetonitrile. The acetonitrile was purified and dried by rectifying initially over calcium hydride, then over diphosphoruspentoxide and finally over calcium hydride again. In each case the first and last 10% of the distillate were discarded. The N,N'-diphenyl-benzidine to be investigated was available p.a. (Merck) and was re-crystallized from n-hexane.

The reference electrode used was a silver wire in contact with 0.1 M AgNo$_3$ is acetonitrile. All measurements were performed at ambient temperature, generally 22° C.

The measuring electrode was polarised by potentiostatic or galvanostatic pulses from a potentiostat. The pulse duration was a few seconds. The change of the extinction E produced by the pulse was measured. Using signal-averaging, the potentiostat was controlled by the signal computer (Nicolet, Mod. 1072) through a pulse generator. After repeating the measurement several times the data stored in the signal computer were recorded by an XY-recorder.

Theoretical Basis

In order to be able to assess the sensitivity of the method, it is firstly important to know how the extinction of a stable electrolysis product depends on rotational speed and radii. The extinction is to be measured in a ring between r$_1$ and r$_2$ outside the disc electrode with radius r$_o$, r$_2$ > r$_1$ ≧ r$_o$.

In the diffusion boundary layer in front of the disc electrode at current density j the concentration of product B drops from the concentration b$_o$ at the electrode at $x=0$ inside the Nernst diffusion boundary layer of thickness $x=\theta$ in a first approximation linearly to concentration $\bar{b}$ within the solution. With the same diffusion coefficients of the initial substance A and the stable product B, b$_o$ cannot become larger than the bulk concentration $\bar{a}$ of substance A. The current density j at the disc electrode is given by $$j = -n_1 F D_A \left(\frac{\partial a}{\partial x}\right)_{x=o} = -n_1 F D_A \frac{a_o - \bar{a}}{\theta_A} \quad (1)$$

or $$j = +n_1 F D_B \left(\frac{\partial b}{\partial x}\right)_{x=o} = +n F D_B \frac{b_o - \bar{b}}{\theta_B} \quad (2)$$

If the solution does not initially contain product b, then $b_o - \bar{b} = \Delta b_o \approx b_o$. The thickness of the diffusion boundary layer at the rotating disc depends on the diffusion coefficients $D_A$ and $D_B$ of the two substances:

$$\theta A = 1.61 D_A^{\frac{1}{3}} \nu^{1/6} \omega^{-\frac{1}{2}} \quad (3)$$

and $$\theta B = 1.61 D_B^{\frac{1}{3}} \nu^{1/6} \omega^{-\frac{1}{2}} \quad (4)$$

In (4) $\omega$ is the angular velocity and $\gamma$ the kinematic viscosity.

From (1)–(4) is obtained $$\Delta b = -\left(\frac{D_A}{D_B}\right)^{\frac{2}{3}} (a_o - \bar{a}) \quad (5)$$

Figure 2B:
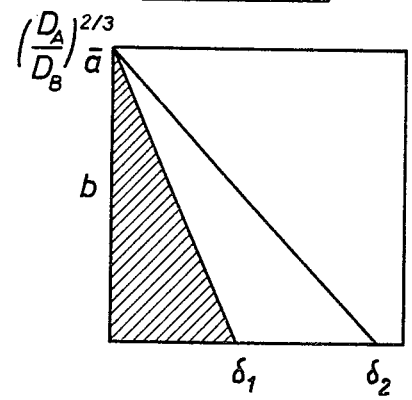

The quantity $m_o$ stored per unit surface area in the boundary layer at $r \leq r_o$ is illustrated for two cases by the area of the hatched triangles in FIGS. 2a and 2b.

FIGS. 2a and 2b show the diagram of the concentration course perpendicular to the rotating disc electrode for two thicknesses $\theta_1$ and $\theta_2$ of the diffusion layer. Product B formed at concentration b and diffusion coefficient D$_B$ in an electrochemical reaction from A with concentration $\bar{a}$ and diffusion coefficient D$_A$.

(a) under galvanostatic conditions at current densities below the diffusion limited current density and (b) under potentiostatic conditions at the diffusion limited current density.

In case (a) with constant disc current below the diffusion limited current we obtain $$m_o = \Delta b \theta_B / 2 = j \theta_B^2 / 2 n_1 F D_B \quad (6)$$

Under potentiostatic conditions in case (b) with diffusion limited current density j$_d$ we obtain $$m_o = \bar{a} \left(\frac{D_A}{D_B}\right)^{\frac{2}{3}} \theta_B / 2 \quad (6b)$$

We obtain from (4) and (6)

$$m_o = 1.30 (\gamma / D_B)^{\frac{1}{6}} \frac{j}{n_1 F \omega} \quad (7a)$$

and from (4) and (6)

$$m_o^g = 0.81 D_A^{\frac{2}{3}} D_B^{\frac{1}{3}} \gamma^{1/6} \bar{a} \omega^{\frac{1}{2}} \quad (7)$$

At a larger distance $r > r_o$ from the electrode the surface concentration $m_o$ in the diffusion boundary layer drops.

For the quantitative solution of this problem using the differential equation of convective diffusion, it is necessary to calculate the concentration course b (r,y) as a function of the radius r and the vertical distance from the disc for initial conditions, which are for $$r > r_o : \left(\frac{\partial b}{\partial y}\right)_{y=o} = 0$$

and for $$r \leq r_o : \left(\frac{\partial b}{\partial y}\right)_{y=o} = j/nFD_B.$$

As in the annular area between the two electrodes of the rotating disc electrode the concentration course at $r > r_o$ depends only on the radius and not on the rotational speed. Therefore for $r > r_o$, $m_o$ differs from (7a) and (7b) only by a collection efficiency k(r), which for $r - r_o < < r_o$ is of the order of magnitude 1.

In the case of validity of Beer's Law the extinction $E_o$ of the stable electrolysis product with the extinction coefficient $\epsilon$ is described under galvanostatic conditions by $$E_o = \epsilon m_o = \epsilon k(r) \cdot 1.30 \left(\frac{\gamma}{D_B}\right)^{\frac{1}{3}} \frac{j}{n_1 F \omega} \quad (8a)$$

and under potentiostatic conditions at the diffusion limited current density by $$E_o{}^{gr} = \epsilon m_o{}^{gr} = \epsilon k(r) \cdot 0.81 D_A{}^{\frac{2}{3}} D_B{}^{-\frac{1}{6}} \gamma^{1/6} \bar{a} \omega^{-\frac{1}{2}} \quad (8b)$$

The collection efficiency k(r) can be experimentally determined if the extinction coefficient, diffusion coefficient and kinematic viscosity are known. If k(r) is known it is possible to determine unknown extinction coefficients because the remaining quantities in (8) are in any case accessible by other methods.

Equation (8) makes it possible to estimate the sensitivity of the method. One may without difficulty measure changes in the extinction of $E = 10^{-3}$. Concentrations of the order of magnitude $b_o = 10^{-5}$ M can be detected for an extinction coefficient $\epsilon = 10^4$ M$^{-1}$cm$^{-1}$, a diffusion coefficient $D = 10^{-5}$ cm$^2$s$^{-1}$, a kinematic viscosity $\gamma = 10^{-2}$ cm$^2$s$^{-1}$ and an angular velocity $\omega = 1$s$^{-1}$. Applying improved measuring techniques the sensitivity can be significantly increased.

In the case of the primary product B reacting further, the extinction is no longer described by (8) and instead it must be calculated separately for each reaction type. If B continues to react in an irreversible reaction of the first order at the disc $$B \xrightarrow{k_1} C + n_2 e^- \quad (9)$$

then we obtain in place of (2)

$$j = b_o(n_2 F k_1 - n_1 F \frac{D_B}{\theta_B}) \quad (10)$$

because due to the irreversibility we set $\bar{b} < < b_o$.

Thus, compared to a stable product the extinction of the product is diminished according to $$E/E_o = m_1/m_o = 1 - n_2 k_1 1.61 \gamma^{1/6}/n_1 D_B{}^{\frac{2}{3}} \omega^{\frac{1}{2}} \quad (11)$$

The precipitation of a sparingly soluble product B can be a heterogenous reaction of the first order. This yields $$j = n_1 F \left[ D_B \frac{b_o - \bar{b}}{\theta_B} + k_1(b_o - b_s) \right] \quad (12)$$

where $b_s$ is the saturation concentration of B. In the case of not too large supersaturations the product essentially only precipitates at the disc electrode because the solution is rapidly diluted in the diffusion boundary layer for $r > r_o$.

This leads to:

$$E_o/E = (1 + k_1 \frac{\theta_B}{D_B}) / [1 + k_1(b_s - \bar{b})n_s F/j] \quad (13)$$

It is possible without difficulty to derive analogous relationships for a heterogeneous reaction of the second order. However, for the precise determination of the rate constants of a homogenous follow-up reaction of the first order, it is necessary to solve the differential equation for the convective diffusion taking into account the reaction. It is to be expected that the relative extinction $E/E_o$ decreases in a linear manner with the logarithm of the angular velocity. Very probably no analytical solution exists for a homogenous reaction of the second order. However, working curves can be calculated by digital simulation. The homogenous reactions of B will be dealt with in greater detail in later research.

Experimental Results

The new method was used for the investigation of the oxidation kinetics of certain aromatic amines. When oxidising N,N'-diphenylbenzidine B in acetonitrile without addition of acid, one obtains in reversible reaction the corresponding semiquinone-imine S $$B \rightleftharpoons SH^+ + e^- \quad U_{\frac{1}{2}} = 0.320 \, V \quad (14)$$

and subsequently quinone-diimine Q $$SH^+ \rightleftharpoons QH_2{}^{++} + e^- \quad U_{\frac{1}{2}} = 0.448 \, V \quad (15)$$

According to Cauquis et al. and according to our own independent measurements, in the neutral medium S is present as a radical cation and Q as a dication with a diquinoid structure.

In the presence of acid the two polarographic waves coalesce into one of double step height as soon as in the kinetically strongly inhibited equilibrium $$B + H^+ \rightleftharpoons BH^+ \quad (16)$$

the cation BH$^+$ is mainly present. BH$^+$ is reversibly oxidised to QH$_2{}^{++}$ according to $$BH^+ \rightleftharpoons QH_2{}^{++} + H^+ + 2e^- \quad (17)$$

Figure 3:
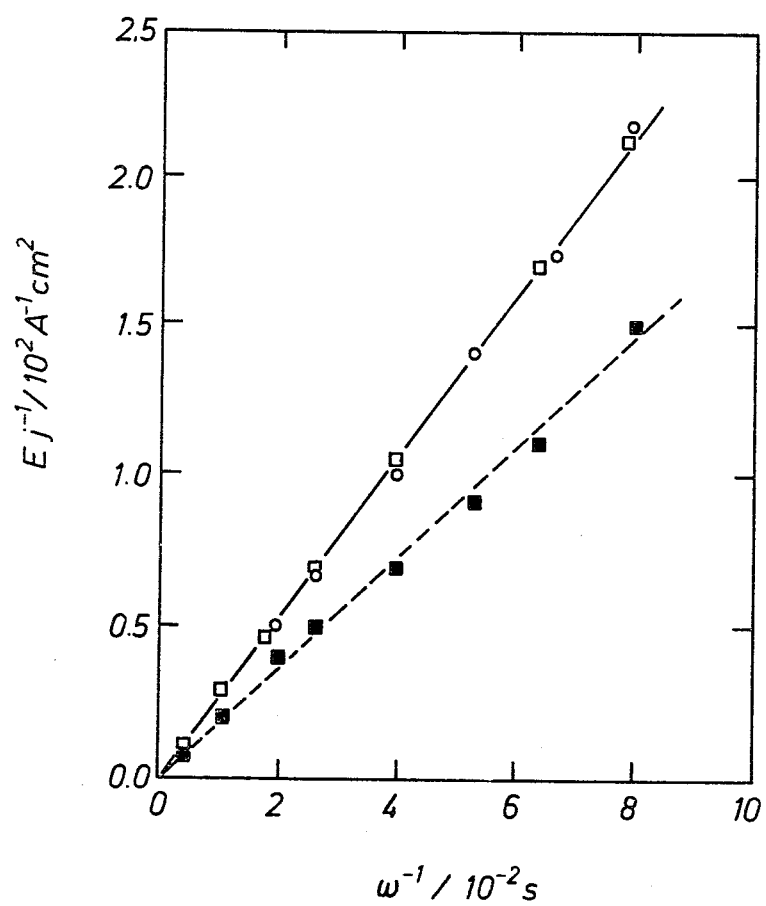
FIG. 3, the dependence of the ratio of extinction E to current density j on the reciprocal angular velocity $\omega$ for the oxidation of N,N'-diphenylbenzidine.

For the oxidation of 0.03 M benzidine in presence of 50 mMHClO$_4$ the half-wave potential was $U_{\frac{1}{2}}=0.640$ V. FIG. 3 shows the extinction of Q at $\lambda=580$ nm as a function of the reciprocal angular veb city. FIG. 3 shows the dependence of the ratio of extinction E to current density j on the reciprocal angular velocity $\omega$ for the oxidation of N,N'-diphenyl-benzidine to quinone-diimine in 0.1 M LiClO$_4$+50 nM HClO$_4$.

Open symbols: Light ring at $r_1=r_o=6.5$ mm to $r_2=7.5$ mm.

Closed symbols: Aperture of diaphragm $r_1=7.8$ mm to $r_2=8.8$ mm.

Squares: $j=75.2$ $\mu$Acm$^{-2}$, Circles: $j=37.6$ $\mu$Acm$^{-2}$.

Measurements with the light ring close to the electrode yielded for $\epsilon_Q=58500$ a collection effieciency $k(r)=0.78$ independent of the selected constant current densities smaller than the diffusion limited current densities. The collection efficiency dropped considerably to $k(r)=0.55$ at a ring located further out with $r_1=7.8$ mm and $r_2=8.8$ mm. The slopes of the lines in FIG. 3 can be determined with average errors between 1 and 2%. The average error of k (r) is mainly due to the uncertainty in the determination of the extinction coefficient with an average error of ±5%. Further smaller sources of error are inaccuracies of weighing, of the kinematical viscosity $\gamma=4.8 \cdot 10^{-3}$ cm$^2$s$^{-1}$ and of the diffusion coefficients $D_{BH+}=D_{QH2++}=7.6 \cdot 10^{-6}$ cm$^2$s$^{-1}$ calculated from the diffusion limited current densities.

Figure 4:
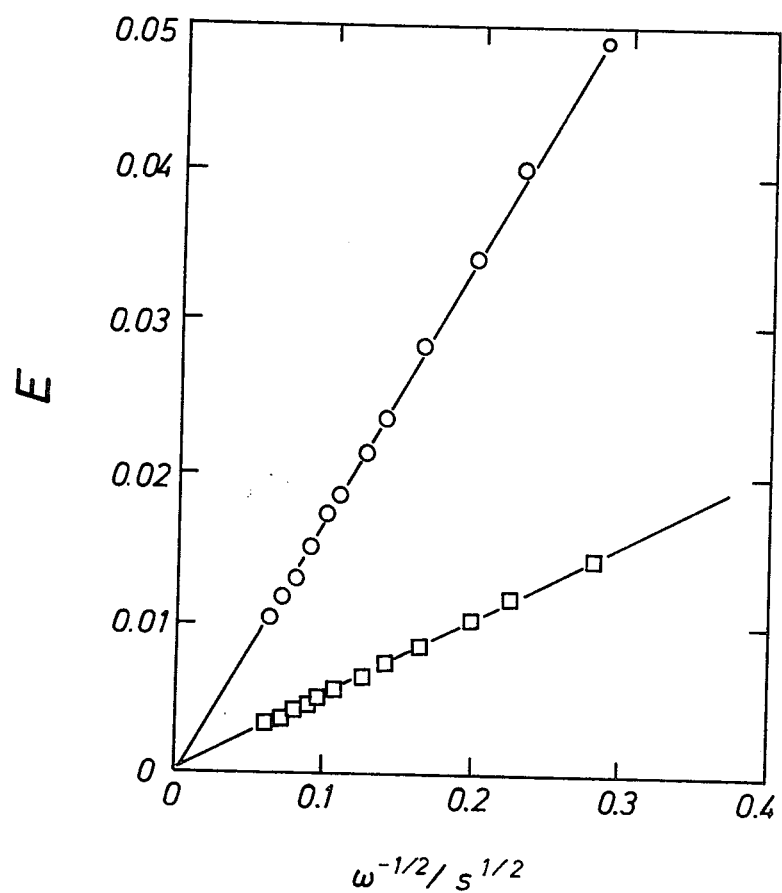
FIG. 4, the dependence of extinction E at the limiting diffusion current on the root of the reciprocal angular velocity $\omega$.

If the diffusion limited current is established under potentiostatic conditions, a linear dependence of the extinction on the reciprocal root of the angular velocity is obtained, as shown in FIG. 4.

FIG. 4 shows relative to the diffusion limited current the dependence of extinction E on the root of the reciprocal angular velocity $\omega$. Light ring at $r_1=r_o=6.5$ mm to $r_2=7.5$ mm, potential of disc electrode $U=0.85$ V, (o) 550 $\mu$M and (□) 170 $\mu$M N,N'-diphenyl-benzidine and 0.1 M LiClO$_4$+50 mM HClO$_4$ in acetonitrile.

For two different concentrations of B, collection efficiencies $k(r)=0.81$ and $k(r)=0.79$ are obtained which within the accuracy of measurement coincide well within the range of those from experiments under galvanostatic conditions.

S is stable in neutral solutions but has a lower solubility than B or Q so that on exceeding the saturation concentration, it is deposited on the disc electrode.

Figure 5:
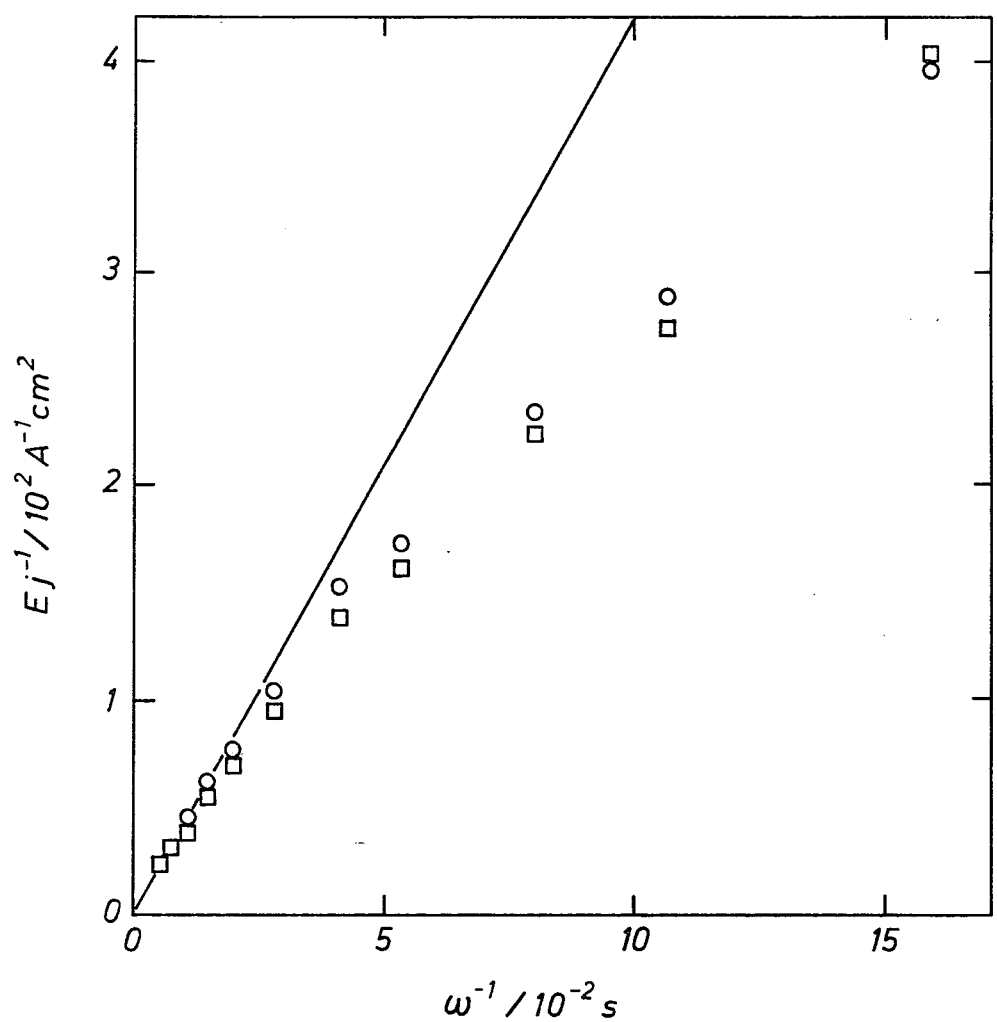
FIG. 5, the ratio of extinction E to current density j as a function of the reciprocal angular velocity $\omega$.

FIG. 5 shows that under galvanostatic conditions in the case of low angular velocities the extinction of S is always lower than expected from the collection efficiency k(r). However, at higher angular velocities a straight line is obtained which with the extinction coefficients $\epsilon_S=46500$ M$^{-1}$cm$^{-1}$ at $\lambda=455$ nm gives the same value $k(r)=0.79$ as was determined from FIGS. 3 and 4. Under these conditions the extinction $E_o$ of a stable product is obtained.

FIG. 5 shows the ratio of extinction E to current density j as a function of the reciprocal angular velocity $\omega$ for the oxidation of $10^{-3}$ M of N,N'-diphenyl-benzidine to semiquinoneimine in neutral 0.1 M LiClO$_4$-solution in acetonitrile at (o) $j=37.6$ $\mu$Acm$^{-2}$ and (□) $j=75.2$ $\mu$Acm$^{-2}$. The line corresponds to the extinction $E_o$ of a stable product.

Figure 6:
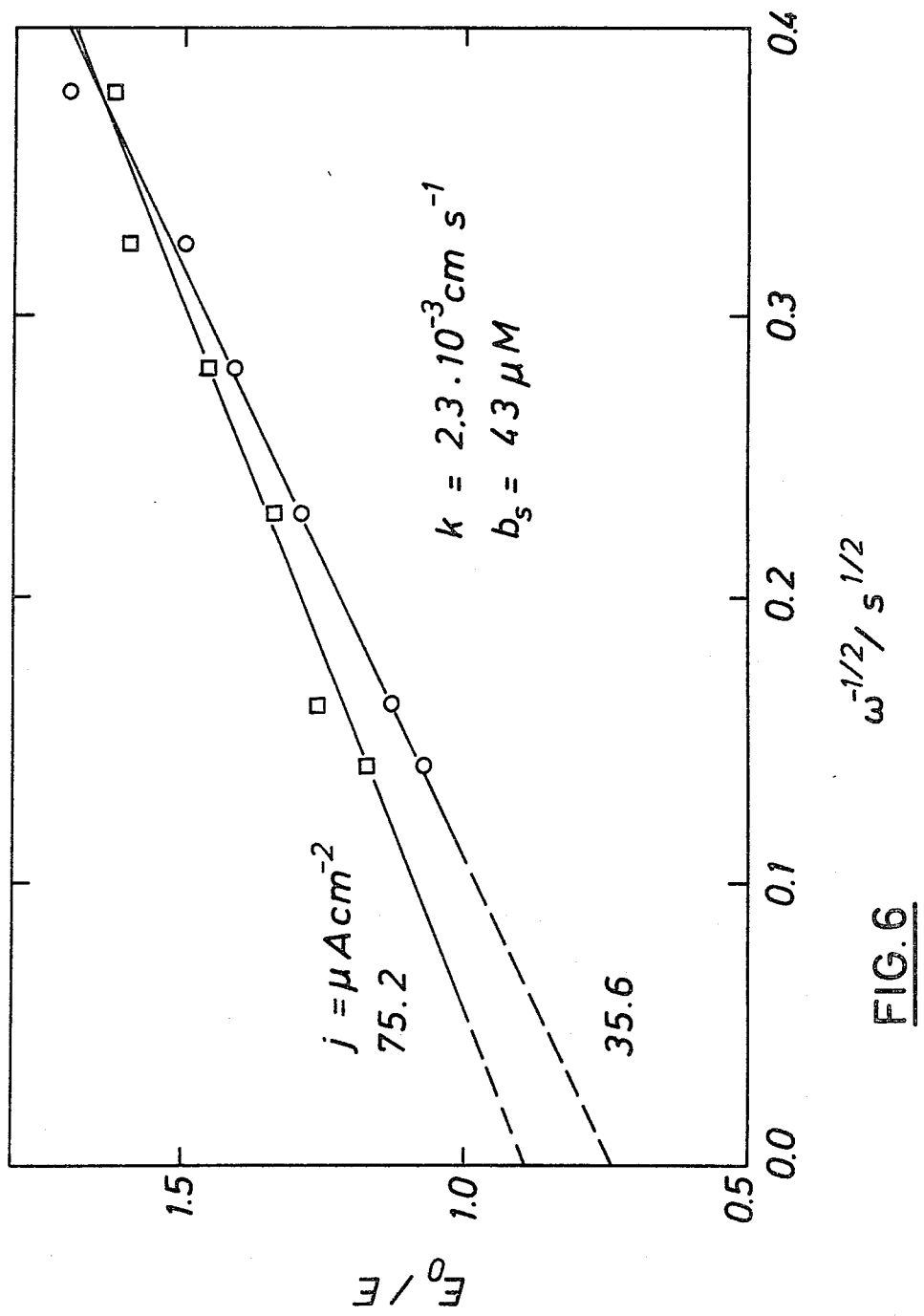
FIG. 6, the ratio of extinction $E_o$ of the stable product to the measured extinction E as a function of the reciprocal root of the angular velocity $\omega$.

If as in FIG. 6 the ratio $E_o/E$ from FIG. 5 is plotted against the root of the reciprocal velocity, then in accordance with (13) one obtains from the slope the rate constant of precipitation $k_1=2.3 \cdot 10^{-3}$ cm s$^{-1}$ and from the intersection with the ordinate and the slope $b_s-\bar{b}=43$ $\mu$M.

FIG. 6 shows the ratio of extinction $E_o$ of the stable product to the measured extinction E as a function of the reciprocal root of the angular velocity $\omega$. Same conditions as in FIG. 5.

As the semiquinone-imine concentration in the solution is negligible, $b_s-\bar{b}$ is essentially equal to the saturation concentration. For high rotational speeds $E_o/E=1$ is observed. This divergence from (13) is due to the fact that when deriving this relationship a disc covered with solid product was assumed. The dissolution of the product leads to $E>E_o$. However in the steady state and at high rotational speeds the electrode is not covered with S due to $b<b_s$.

The oxidation of diphenyl-benzidine B also provides an example for a rapid homogenous reaction of the second order. At positive potentials corresponding to the limiting current of the oxidation of B to Q, quinone-diimine Q reacts in neutral solution with B to give semiquinone-imine S:

$$Q+B\rightarrow 2 S \qquad (18)$$

Figure 7:
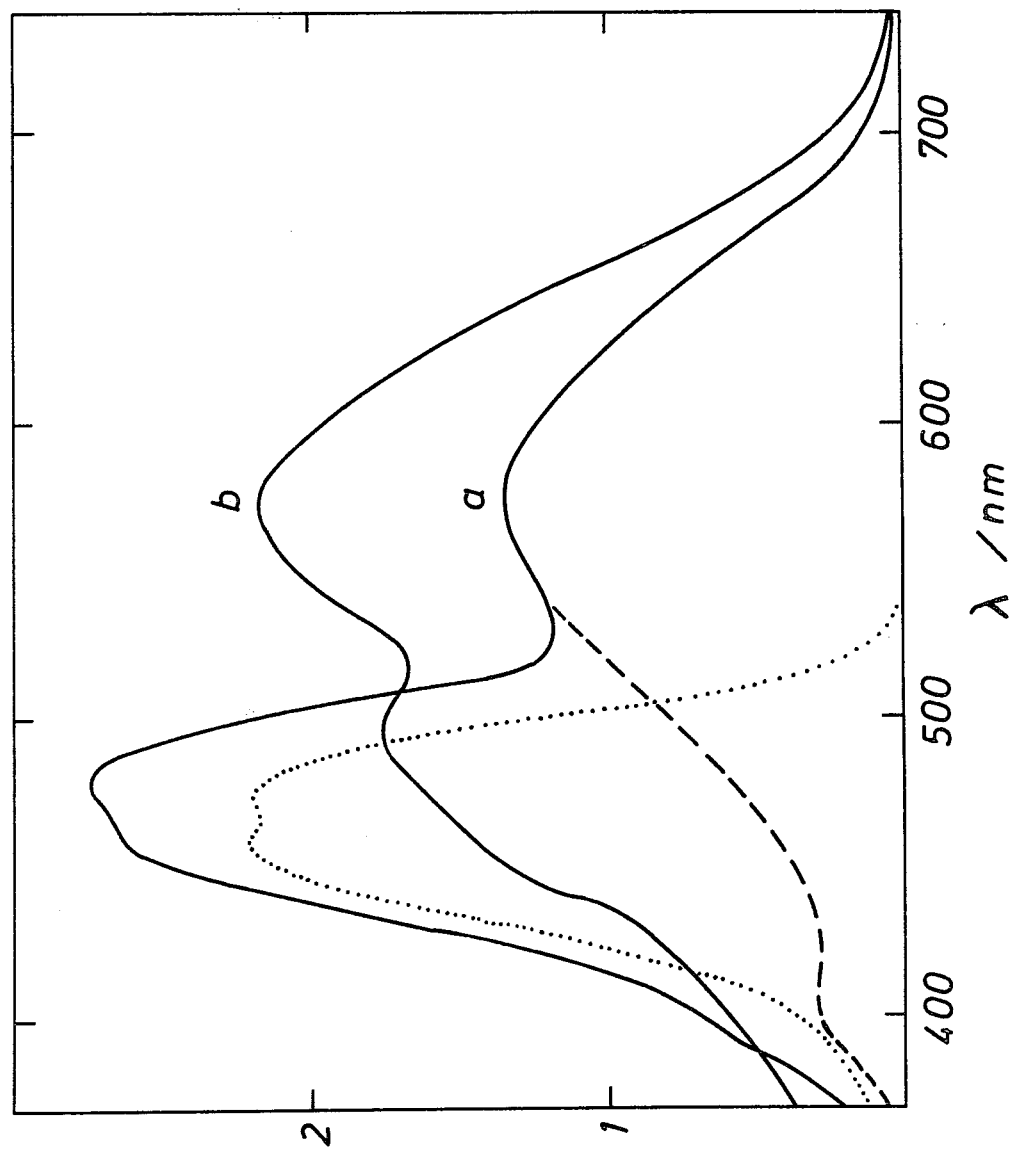
FIG. 7, experimental spectra of oxidation products of N,N'-diphenyl-benzidine.

Reaction (18) takes place within the diffusion boundary layer. FIG. 7 gives normalized spectra at two different angular velocities.

FIG. 7 shows experimental spectra of oxidation products of N,N'-diphenyl-benzidine in 0.1 M LiClO$_4$/CH$_3$CN at different angular velocities $\omega$, limiting current densities j at the potential of the disc electrode $U=0.62$ V, and angular velocities (a)$\omega=31.5$s$^{-1}$ and (b)$\omega=189$s$^{-1}$. The dotted line shows the spectrum of semiquinone-imine with absorption maxima at $\lambda=455$ and 480 nm, while the broken line indicates the spectrum of quinone-diimine with absorption maxima at $\lambda=405$ and 580 nm.

At higher angular velocities between 80 and 85% are present in the form of the primary product Q, while at lower angular velocities only 45 to 50% are present. A rate constant of the order of $10^6$M$^{-1}$s$^{-1}$ can be estimated for the reaction (18). Ignoring the concentration profile perpendicular to the disc for simplicity, average concentrations were assumed in the boundary layer and average reaction times were estimated from the ratios of radii and from the rotational speed.

In order to analyse the spectra quantitatively, the overlapping absorption bands of substances B and S were separated. This is easy in the present example because the spectra of the pure substances are known. In other cases it is for example possible to determine the unknown absorption spectrum of a short lived intermediate from the known shapes of the spectra of stable reagents and the overall spectra measured at different angular velocities and current densities. Even if several unknown products are present, it is in principle possible to separate the overall spectra into spectra of the individual products.

Figure 8:
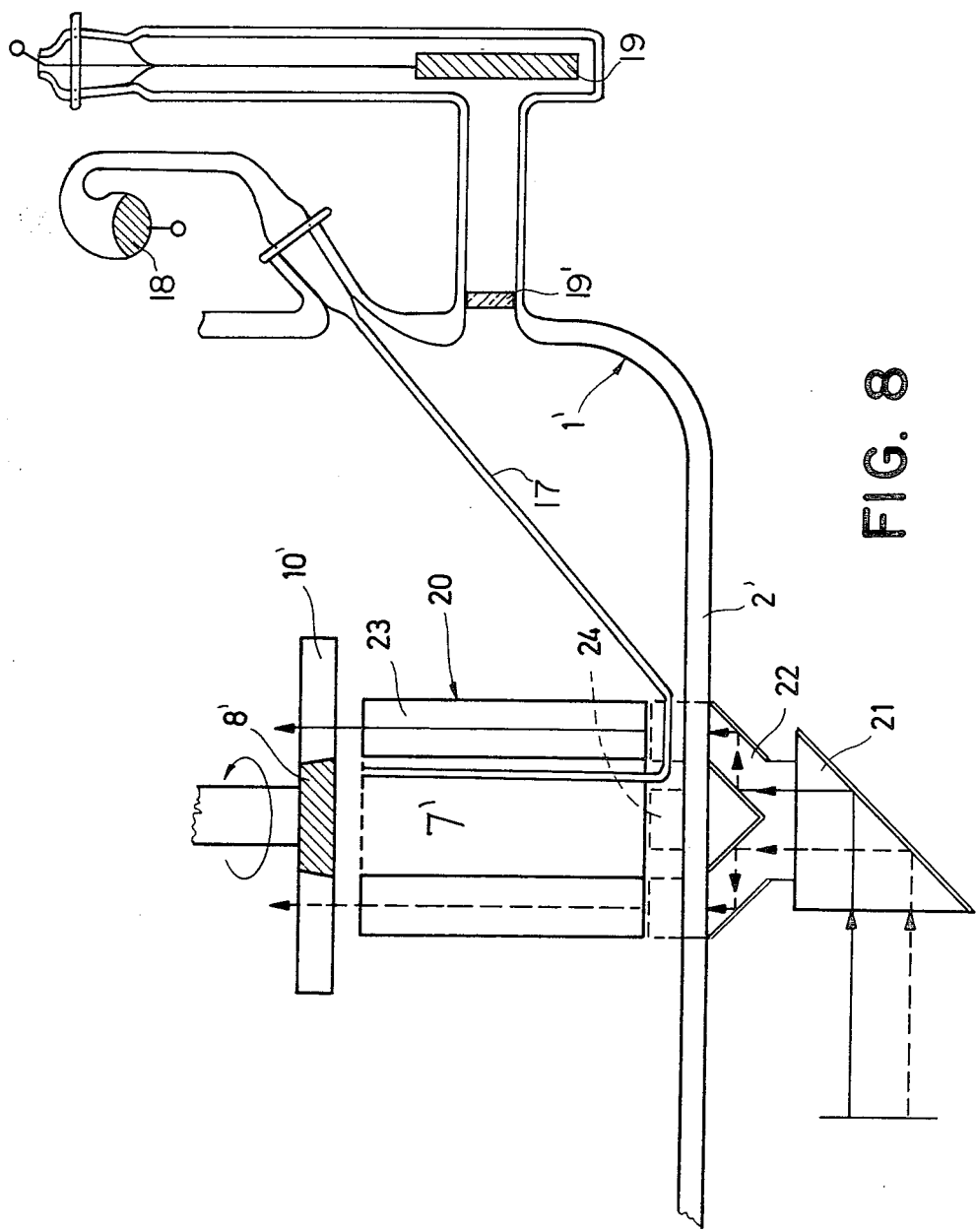
FIG. 8, another embodiment of the apparatus according to the invention.

In the other embodiment of the apparatus according to the invention shown in FIG. 8, the cup-shaped lower part 2' of reaction vessel 1' is made from quartz glass. Rotating electrode 8', optical ring 10', the drive of the electrode and receiver are constructed in much the same way as in the embodiment of FIG. 1. However, in this case the light transmitter 20 is a prism optics which is essentially located outside the reaction vessel. Underneath the reaction vessel the light passes laterally into a prism 21 from which it is deflected vertically upwards in the direction of the bottom of the vessel. An adjacent prism 22 with a conical inner and outer surface located directly below the vessel wall 2' converts the circular cross section of the light into a ring-shaped one which is passed through the vessel wall. The light ring is further transmitted through a body 23 in the form of a hollow cylinder which has a higher index of refraction than the surrounding solution. Hollow cylinder 23 is placed at a small distance above the bottom of the vessel and is coaxial to the rotation axis of electrode 8', and coaxial to prism 22. The distance is sufficient to allow circulation of the electrolyte solution through the inner area 7' of the hollow cylinder towards the rotating electrode 8', and said distance approximately corresponds to the distance between the light exit point at the top of body 23 and the optical ring 10'. The hollow cylinder 23 can also be mounted directly on the base of the vessel as indicated by the broken lines in FIG. 8. Lateral openings 24 in hollow cylinder 23 permit the passage of the solution. Light is partly transmitted directly through the foot of hollow cylinder 23 at the bottom of the vessel and partly via the solution in the lateral openings. The reflection losses should only be slightly higher with this modification.

The invention is not limited to the embodiments described and represented hereinbefore and various modifications can be made thereto without passing beyond the scope of the invention.

What is claimed is:

1. A method for the spectrophotometric investigation of products of electrochemical reactions in a solution containing at least one dissolved initial product, comprising the steps of:

directing the solution essentially axially towards a rotating disc electrode surrounded by a homogeneous optically translucent ring, the flow being reversed at the rotating electrode into an outwardly directed radial flow;

determining the concentration of products formed at the electrode by passing monochromatic light through the radial product flow and the optically translucent ring and measuring the light absorption; and, performing the measurement under quasi-stationary conditions by permitting current for the electrochemical reaction to flow without interruption for at least approximately 0.5 seconds prior to making the measurement.

2. A method according to claim 1, wherein the current is permitted to flow for a period of at least approximately 1 to 10 seconds without interruption prior to making the measurement.

3. A method according to claim 1, wherein the thickness of the liquid layer to be irradiated is kept smaller than 50 to 100 times the thickness of the Nernst boundary layer between the electrode and optical ring.

4. A method according to claim 1, wherein the liquid layer between the disc electrode and the exit of the monochromatic light is kept at a thickness of approximately 1 to 10 mm.

5. A method according to claim 1, wherein the liquid flow is passed as a circular flow through the center of an annular body so that it rises in the direction of the electrode and outside the ring is returned downwards to the center of the annular body.

6. A method according to claim 1, wherein the surface level of the solution is approximately at the same level as the disc electrode.

7. A method according to claim 1, wherein the disc is rotated at a speed of at least half a revolution per second to 150 revolutions per second.

8. A method according to claim 1, wherein determinations of zero points are performed in the currentless state alternately with repeated measurements during the reaction.

9. A method according to claim 1, further comprising the steps of varying at least one of the rotational speed of the electrode, the current intensity, the temperature and concentration of the solution and the wave length of the monochromatic light; and, drawing conclusions on the type of reaction from the dependence of the light absorption on the indicated parameters.

10. A method according to claim 1, wherein current densities in the microampere to milliampere/$cm^2$ range are used for investigating reaction products, and current densities in the milli ampere/$cm^2$ range are used for investigating unstable reaction products.

11. A method according to claim 1, wherein light in the wave length range of 180 to 1000 nanometres is used.

12. A method according to claim 1, wherein the measured absorption values are integrated.

13. A method according to claim 1, wherein the measured absorption values are measured with a lock-in amplifier at a freely selectable frequency of light pulses, in the range of 10 to 1000 Hz.

14. A spectrophotometer, comprising:

a vessel for holding a solution, the solution containing at least one dissolved initial product;

a flat rotationally symmetrical electrode, having a precisely circular edge, rotatable around its longitudinal axis;

a homogeneous optically translucent ring surrounding the electrode, the ring having a plane-parallel construction, being optically compact, and forming a jointless and planar transition to the precisely circular edge of the rotating electrode;

a light transmitter pointing towards the electrode and a light receiver on the opposite side of the optically translucent ring;

a counter-electrode to the rotating electrode; and, a reference electrode for measuring the electrical cell voltage.

15. An apparatus according to claim 14, wherein the rotating electrode and the optically translucent ring are constructed as a disc having a flat underside, the rotation axis being perpendicular to the disc.

16. An apparatus according to claim 14, wherein the rotating electrode is constructed as a ring electrode with an insulated center.

17. An apparatus according to claim 14, wherein the optically translucent ring is made in one piece, from quartz glass.

18. An apparatus according to claim 14, wherein all components located in the light path are made from material which is permeable to ultra-violet light.

19. An apparatus according to claim 14, wherein the radial thickness of the optical ring is at least approximately 1 mm.

20. An apparatus according to claim 14, wherein the diameter of the optical ring is approximately 10 to 50 mm.

21. An apparatus according to claim 14, wherein the thickness of the optical ring is approximately 1 to 10 mm in the direction of the light path.

22. An apparatus according to claim 14, wherein the electrode is made from a corrosion-resistant material.

23. An apparatus according to claim 22, wherein the corrosion-resistant material is a platinum-iridium alloy having approximately 10% iridium.

24. An apparatus according to claim 14, wherein the rotating electrode has a diameter of approximately 1 to 50 mm and an area of approximately 0.01 to 10 cm$^2$.

25. An apparatus according to claim 14, further comprising a magnetic coupling for driving the rotating electrode.

26. An apparatus according to claim 14, wherein the optical transmitter is at a distance of approximately 1 to 10 mm from the optical ring.

27. An apparatus according to claim 14, wherein both the transmitter and the receiver are fixed with reference to the rotational movement of the electrode.

28. An apparatus according to claim 14, wherein the receiver is at a distance of approximately 0.5 to 10 mm from the optical ring.

29. An apparatus according to claim 14, wherein the rotation axis of the rotating electrode is arranged vertically, the transmitter being arranged below the electrode and the receiver above the electrode.

30. An apparatus according to claim 14, wherein at least one of the light transmitter and the receiver is arranged within the vessel, is essentially annular, and has an axis coaxial to the rotation axis of the electrode.

31. An apparatus according to claim 14, wherein the transmitter and receiver have a substantially annular optical cross-section, the dimensions of which correspond essentially to the area of the optical ring.

32. An apparatus according to claim 14, further comprising an adjustable optical diaphragm between the optical ring and the receiver.

33. An apparatus according to claim 14, wherein the light receiver and transmitter are equipped with optical cables.

34. An apparatus according to claim 14, wherein at least the transmitter comprises an optical prism, light reaching the transmitter through a transparent wall of the vessel.

35. An apparatus according to claim 14, wherein the transmitter and the receiver are equipped with adjusting devices.

36. An apparatus according to claim 14, wherein the transmitter and the receiver are connected to a monochromator arranged outside the vessel.

37. An apparatus according to claim 14, further comprising an interchangeable optical diaphragm between the optical ring and the receiver.

* * * * *

UNITED STATES PATENT AND TRADEMARK OFFICE
CERTIFICATE OF CORRECTION

PATENT NO. : 4,252,617
DATED : February 24, 1981
INVENTOR(S) : KONRAD HEUSLER and HEINER DEBRODT It is certified that error appears in the above-identified patent and that said Letters Patent are hereby corrected as shown below:

At Col. 6, line 52, the formula designated as "(6)" should be designated --6(a)--, and the formula itself should read $$-- m_0 = \Delta b \theta_B/2 = j\theta_B^2/2n_1 FD_B --$$

instead of $$" m_0 = \Delta b \theta_B/2 = j\theta_B^2/2n_1 FD_B "$$

At Col. 6, the formula designated as "(7)" should be designated --7(b)--, and the formula itself should read $$-- m_0^{gr} = 0.81 \, D_A^{\frac{2}{3}} D_B^{\frac{1}{3}} \gamma^{\frac{1}{6}} \bar{\sigma} \omega^{-\frac{1}{2}} --$$

instead of $$" m_0^g = 0.81 \, D_A^{\frac{2}{3}} D_B^{\frac{1}{3}} \gamma^{\frac{1}{6}} \bar{\sigma} \omega^{\frac{1}{2}} "$$

UNITED STATES PATENT AND TRADEMARK OFFICE
CERTIFICATE OF CORRECTION

PATENT NO. : 4,252,617

DATED : February 24, 1981

INVENTOR(S) : KONRAD HEUSLER and HEINER DEBRODT

It is certified that error appears in the above-identified patent and that said Letters Patent are hereby corrected as shown below:

At Col. 7, line 38, in the formula designated "8(b)", "0,81" should be --0.81--.

At Col. 9, line 4, "veb city" should be --velocity--.

Signed and Sealed this

First Day of September 1981

[SEAL]

Attest:

GERALD J. MOSSINGHOFF

Attesting Officer     Commissioner of Patents and Trademarks